United States Patent
Maki et al.

(10) Patent No.: US 6,579,286 B1
(45) Date of Patent: *Jun. 17, 2003

(54) LASER IRRADIATION APPARATUS

(75) Inventors: Shin Maki, Kanagawa-ken (JP); Shigenobu Iwahashi, Kanagawa-ken (JP)

(73) Assignee: Terumo Kabushiki Kaisha, Tokyo (JP)

( * ) Notice: Subject to any disclaimer, the term of this patent is extended or adjusted under 35 U.S.C. 154(b) by 126 days.

This patent is subject to a terminal disclaimer.

(21) Appl. No.: 09/635,443

(22) Filed: Aug. 11, 2000

(30) Foreign Application Priority Data

Aug. 13, 1999 (JP) .............................. 11-228960

(51) Int. Cl.[7] .............................................. A61B 18/20
(52) U.S. Cl. .............................. 606/17; 606/10; 606/15
(58) Field of Search .............................. 606/3, 7, 10–18

(56) References Cited

U.S. PATENT DOCUMENTS

| 4,445,892 A | * 5/1984 | Hussein et al. ................ 606/7 |
| 4,932,956 A | 6/1990 | Reddy et al. |
| 4,932,958 A | 6/1990 | Reddy et al. |
| 5,207,672 A | 5/1993 | Roth et al. |
| 5,292,320 A | 3/1994 | Brown et al. |
| 5,496,308 A | 3/1996 | Brown et al. |

FOREIGN PATENT DOCUMENTS

| EP | 0 673 627 | 9/1995 |
| JP | 6-154239 | 6/1994 |
| WO | 92/04934 | 4/1992 |
| WO | 93/04727 | 3/1993 |

* cited by examiner

Primary Examiner—David M. Shay
(74) Attorney, Agent, or Firm—Burns, Doane, Swecker & Mathis, LLP

(57) ABSTRACT

A laser irradiation apparatus including a long and slender main body, an optical fiber, a drive unit, and a reflector. The optical fiber provided is slidable inside the main body, and has a proximal end through which a laser ray is introduced and a distal end through which the laser ray is emitted. The drive unit causes the optical fiber to reciprocate in a longitudinal direction of the main body. The reflector is connected to the optical fiber and has a reflection plane for reflecting the laser ray emitted from the distal end of the optical fiber for reciprocating together with the optical fiber. The reflection plane changes its reflecting angle in accordance with the reciprocating motion of the optical fiber.

19 Claims, 8 Drawing Sheets

LASER IRRADIATION APPARATUS

BACKGROUND OF THE INVENTION

1. Field of the Invention

The invention relates to an apparatus for treating tumors such as cancers or diseases such as benign prostatic hyperplasia by means of irradiating a vital tissue with a laser ray.

2. Description of the Related Art

A treatment technique has been known wherein a lesional region is shrunk or eliminated by alterating, sphacelating, coagulating, cauterizing and evaporating the tissue in the lesional region by means of irradiating it with a laser ray using a laser irradiation apparatus. The laser irradiation apparatus is long and slender and is left in a vital tissue by insertion into boy lumens such as blood vessels, urethra and abdominal cavity, or puncture of an organ, or a small discission.

In such a technique, the surface layer of a vital tissue or a lesional region in its vicinity is irradiated directly with a laser ray. In order to heat a lesional region located at a deep spot in a vital tissue to a sufficient temperature, it is required to apply a laser ray of a relatively large output. It may possibly involve a danger of damaging normal tissues such as a surface layer.

International Publication No. WO 93/04727 discloses a technique of coagulating and shrinking tumors or a portion of the prostate by means of the laser irradiation. This technique uses a balloon, through which cooling liquid is circulated, to cool the tissue to be protected. However, because the laser emitting unit is fixed, the laser power has to be limited, which results in the inconvenience of the reatment being too long.

Unexamined Publication No. JP-A-6-154239 discloses a laser irradiation apparatus to be inserted into the urethra in order to treat benign prostatic hyperplasia. The apparatus includes a plurality of irradiation units to be placed at different positions. The laser rays irradiated from these irradiation units simultaneously converge on a target site in a deep lesional region to generate a sufficient amount of heat to shrink the lesional tissue. The temperatures of the vicinities of the target site are higher than the regions where the laser rays do not overlap. However, since paths of the laser rays are fixed, a certain region is created in the vicinity of the surface layer of the urethra where the laser rays do not overlap but the temperature is slightly higher. This phenomenon disadvantageously affects the protection of the surface layer of the urethra. Thus, the apparatus is not perfect from the standpoint of treating only the deep lesional region while minimizing the damage to the surface layer.

SUMMARY OF THE INVENTION

In a broader sense the object of the invention is to provide an apparatus capable of effectively irradiating a deep lesional region with a laser ray while preventing damages to the normal tissue to be protected easily and securely.

It is more specific object of this invention to provide a laser irradiation apparatus including a long and slender main body, an optical fiber, a drive unit, and a reflector. The optical fiber provided is slidable inside the main body, and has a proximal end through which a laser ray is introduced and a distal end through which the laser ray is emitted. The drive unit causes the optical fiber to reciprocate in a longitudinal direction of the main body. The reflector is connected to the optical fiber and has a reflection plane for reflecting the laser ray emitted from the distal end of the optical fiber for reciprocating together with the optical fiber. The reflection plane changes its reflecting angle in accordance with the reciprocating motion of the optical fiber.

The objects, features, and characteristics of this invention other than those set forth above will become apparent from the description given herein below with reference to preferred embodiments illustrated in the accompanying drawings.

DETAILED DESCRIPTION OF THE PREFERRED EMBODIMENT

The embodiments of this invention will be described below with reference to the accompanying drawings.

Figure 1:
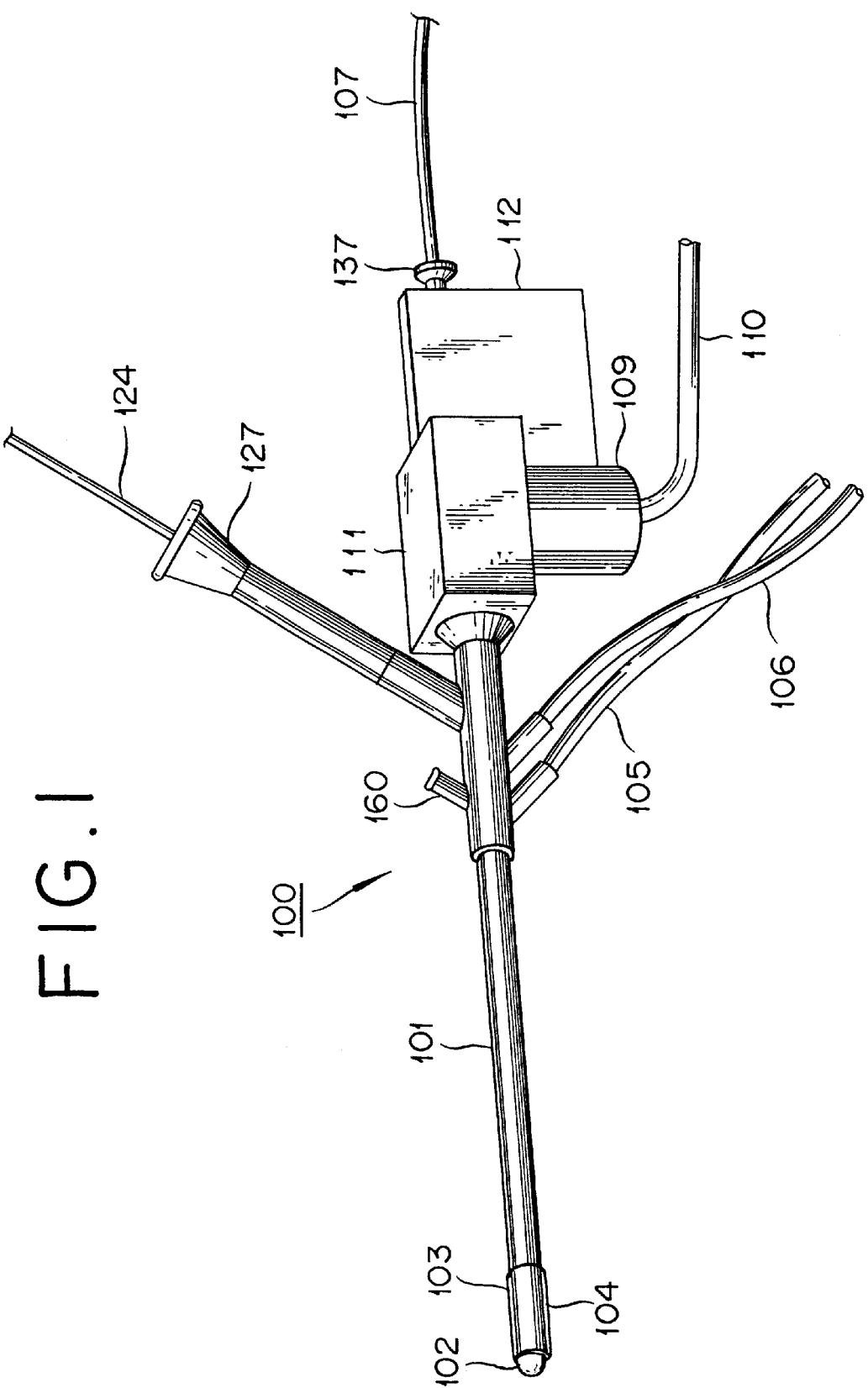
FIG. 1 is a schematic illustration of a laser irradiation apparatus in accordance with the preferred embodiment of the invention.
Figure 2:
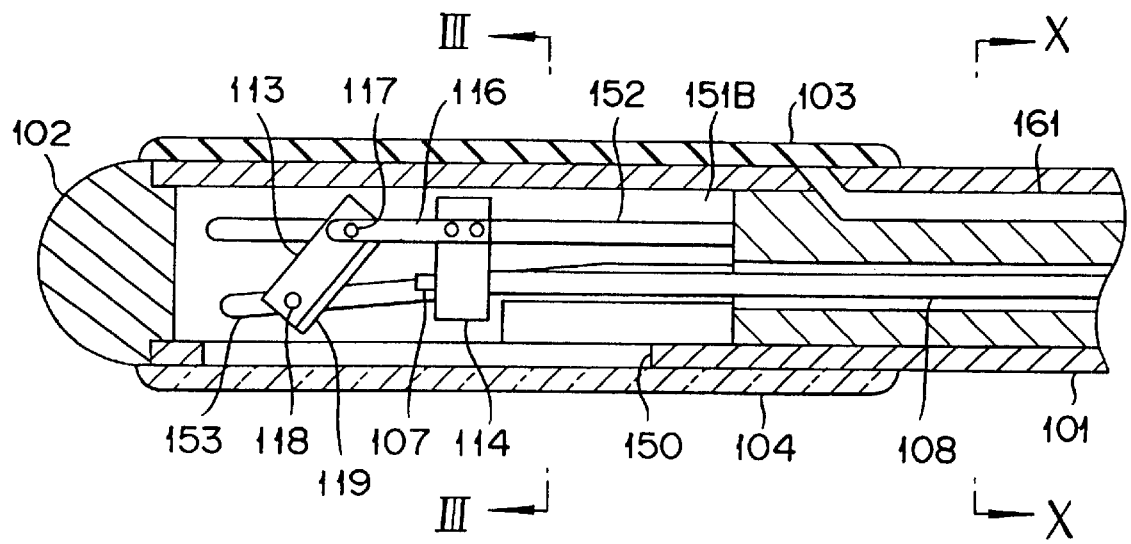
FIG. 2 is a cross sectional view of assistance in explaining the structure of a distal end of the main body of the laser irradiation apparatus.
Figure 3:
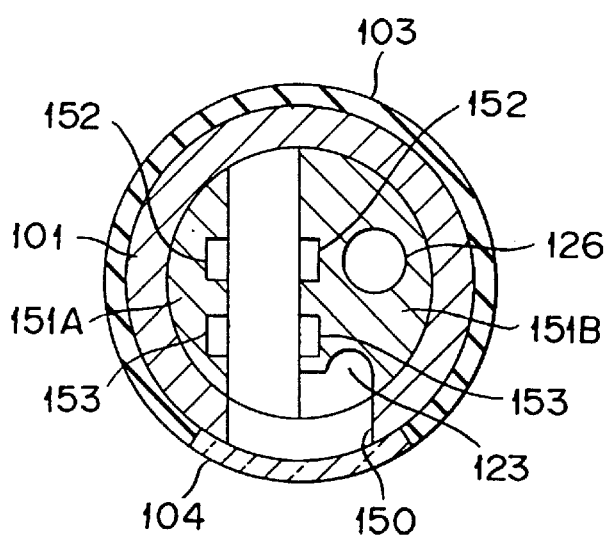
FIG. 3 is a cross sectional view taken on line III—III of FIG. 2.

The laser irradiation apparatus 100 shown in FIG. 1 through FIG. 3 is a side emitting type apparatus and is intended to be used for the treatments of vital tissues, for example, benign prostatic hyperplasia. For the sake of clarity of description, moving parts are not shown in FIG. 3.

As shown in FIG. 1, the apparatus 100 roughly consists of a long and slender main body 101 made of a tube-like member; a drive unit 109; a cam box 111; a buffer device 112; and an endoscope 124, and is connected to a laser generator, a cooling liquid circulating device and a power source, all of which are not shown in the drawing.

The main body 101 is made of a hard tube like member of, for example, metals such as stainless steel. Tubes defining lumens are fixed to portions on the proximal side of the main body 101. A front cap 102 for sealing and a window 150, which is an opening for the laser ray to pass, are provided at the distal end of the main body 101. Moreover, a pair of wall members 151 (151A and 151B) are fixedly provided within the distal end of the main body 101 to define the inner space of the distal end of the main body 101.

Figure 4:
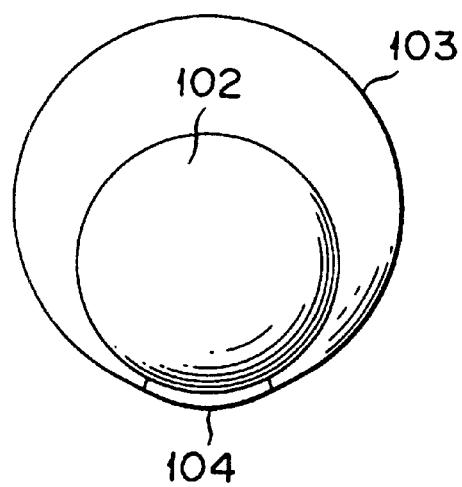
FIG. 4 is a front view of assistance in explaining an expanded condition of a balloon of the laser irradiation apparatus.

In order to protect the window 150, a cover 104 is glued onto the surface of the distal end of the main body 101. A balloon 103 is provided covering the periphery of the distal end of the main body 101 except the areas of the window 150 and the cover 104, through which the laser ray passes. The balloon 103 is made of a plastic film and is expandable. The balloon 103 communicates with the port 160 via the lumen 161, and expands because of the liquid supplied through the port 160 to perform a function of pressing the side opposite to the balloon 103, or the side where the window 150 is formed, against the surface of the vital tissue. FIG. 4 is the front view of the distal end of the main body 101 when the balloon 103 is expanded.

An optical fiber 107 that transmits the laser ray is provided inside the main body 101. The optical fiber 107, except its distal portion located inside the distal end of the main body 101, is entirely covered by a protective pipe 108 made of stainless steel in order to prevent it from damage or bending. The proximal end of the optical fiber 107 is connected to the laser generator via an optical connector.

Next, a laser emitting unit provided within the distal end of the main body 101 will be described.

Figure 5:
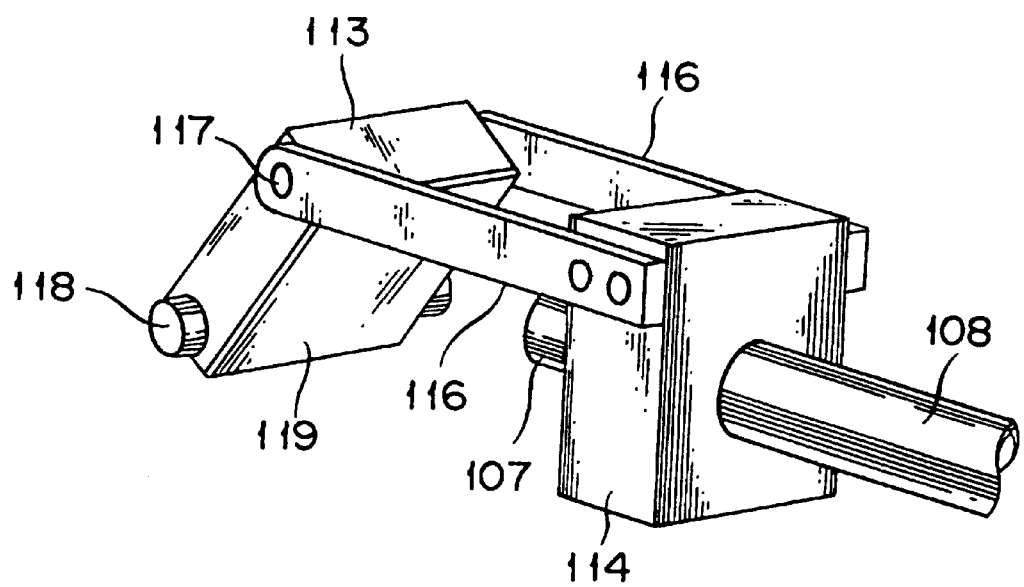
FIG. 5 is a perspective view of assistance in explaining a laser emitting unit of the laser irradiation apparatus.

The laser emitting unit includes, as shown in FIG. 5, a reflector 113, a pair of arms 116, and a fixing member 114. On the wall members 151, a pair of guide grooves 152 and a pair of guide grooves 153 are formed for the laser emitting unit (see FIG. 3).

The reflector 113 has a reflection plane 119 to direct the laser ray sideways, and is positioned in front of the distal portion of the optical fiber 107. The reflection plane 119 should preferably be a film formed by laminating, vapor depositing or plating metals such as gold, or a multiple-layer film of dielectric materials. The multiple-layer film is formed by vapor depositing reciprocally a high refractive index dielectric substance and a low refractive index dielectric substance several times. High refractive index dielectric substances are typically $Al_2O_3$, $ZrO_2$, $TiO_2$ and $CeO_2$, and low refractive index dielectric substances typically $MgF_2$ and $SiO_2$.

On both sides of the reflector 113 formed are a first protrusion 117 and a second protrusion 118. The first protrusion 117 connects to one end of the arm 116. Said end of the arm 116 forms a hinge mechanism that is rotatable around the first protrusion 117 as a shaft. On the other hand, the other end of the arm 116 is attached to the side of the fixing member 114 attached to the distal end of the optical fiber 107. Consequently, the laser emitting unit reciprocates together with the optical fiber, while maintaining the relative distance between the reflector 113 and the distal end of the optical fiber 107 approximately constant.

The arm 116 slidably engages with the guide groove 152 provided on the wall member 151. The guide groove 152 is parallel with the axial direction of the main body 101 and serves to stabilize the performance of the reciprocating motion of the optical fiber 107 and the reflector 113.

The second protrusion 118 engages with the guide groove 153 provided on the wall member 151. The guide groove 153 is not parallel with the axial direction of the main body 101 and the guide groove 152 except the proximal end of the groove 153. The space between the guide groove 153 and the groove 152 widens as it moves from the proximal side to the distal side. The proximal end of the guide groove 153 is located outside of the reciprocating motion range of the reflector 113, its length is several millimeters, and is parallel to the guide groove 152. This parallel portion is provided for the purpose of making it easier to insert movable components into the main body 101 during the manufacture.

Figure 6:
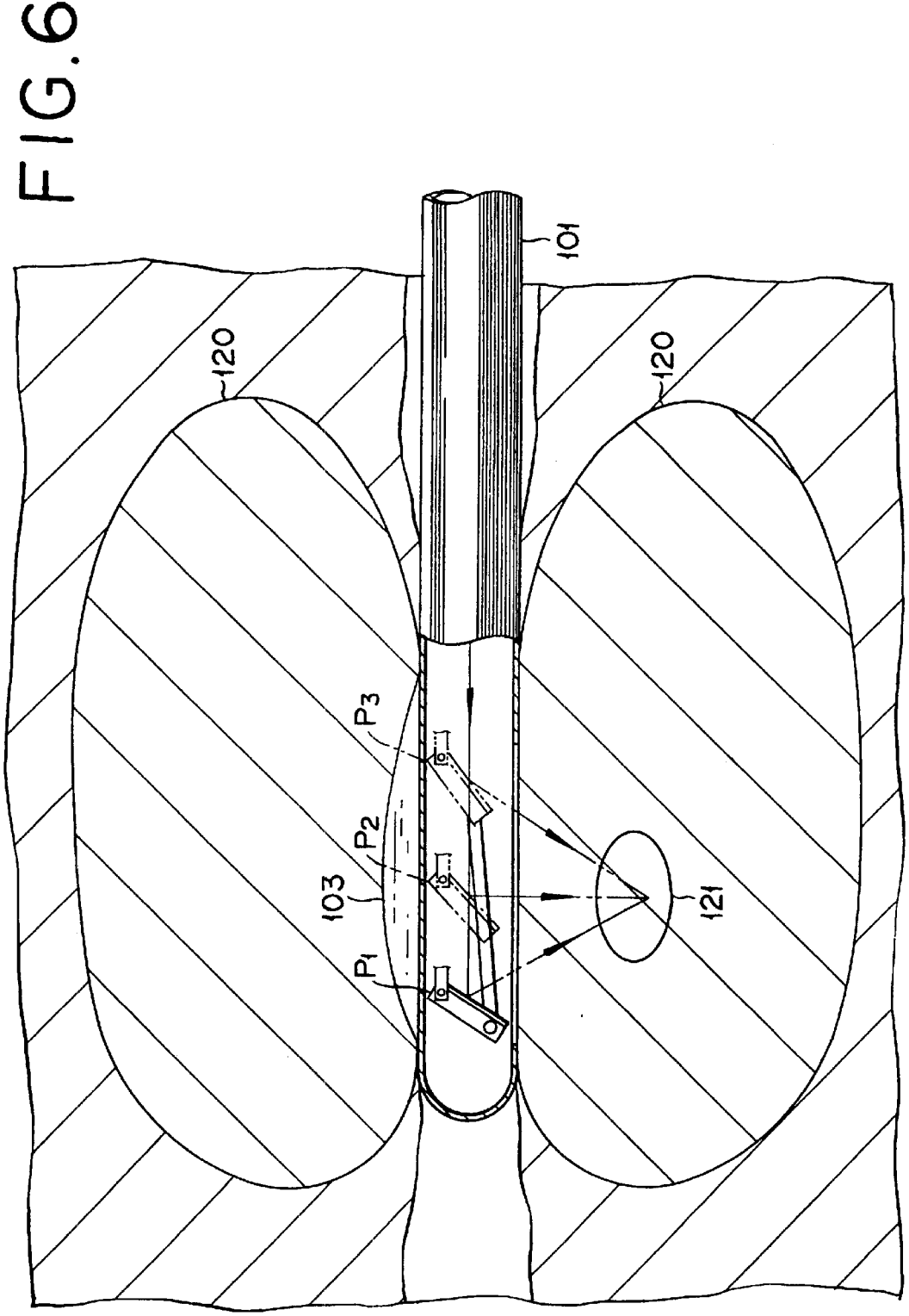
FIG. 6 is a conceptual illustration of assistance in explaining paths of the laser ray when a reflector of the laser emitting unit is reciprocating while changing the reflective angle accordingly.

Thanks to said structure of the guide grooves 152 and 153, the reflector 113 travels back and forth while changing the reflection angle continuously as shown in FIG. 6. More specifically, the reflector 113 becomes approximately vertical relative to the axial direction of the main body 101 when it is located at the distal position P1. Therefore, the sum of the incident angle and the reflection angle of the laser ray is smaller than 90 degrees. On the other hand, the reflector 113 becomes approximately parallel to the axial direction of the main body 101 when it is located at the proximal position P3. Therefore, the sum of the incident angle and the reflection angle of the laser ray is greater than 90 degrees. Moreover, when the reflector 113 is located at the intermediate position P2 between the distal position P1 and the proximal position P3, the sum of the incident angle and the reflection angle of the laser ray is 90 degrees. Consequently, as the reflector 113 travels moves back and forth changing the reflecting angle continuously, the laser ray emitting position moves constantly, while paths of the laser ray converge within the target site 121.

Thus, the laser emitting unit reciprocates accompanying the optical fiber, maintaining the relative position between the distal portion of the optical fiber and the reflector 113 approximately constant. As a result, the spot diameter of the laser ray can be stabilized without using any special optical system. Moreover, since the structure of the apparatus is simple, it is easier to manufacture and it is expected to have a smaller chance of breakdown.

Figure 7:
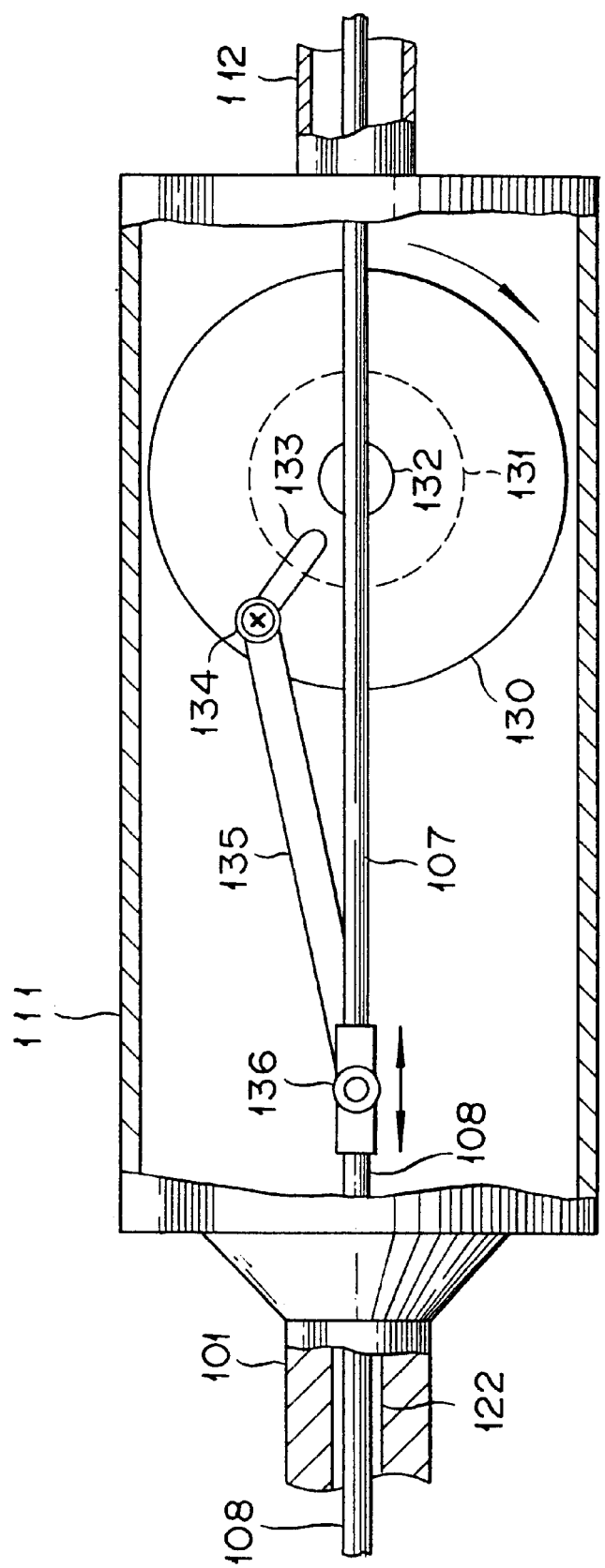
FIG. 7 is a partially cutaway plan view of a cam box of the laser irradiation apparatus.
Figure 8:
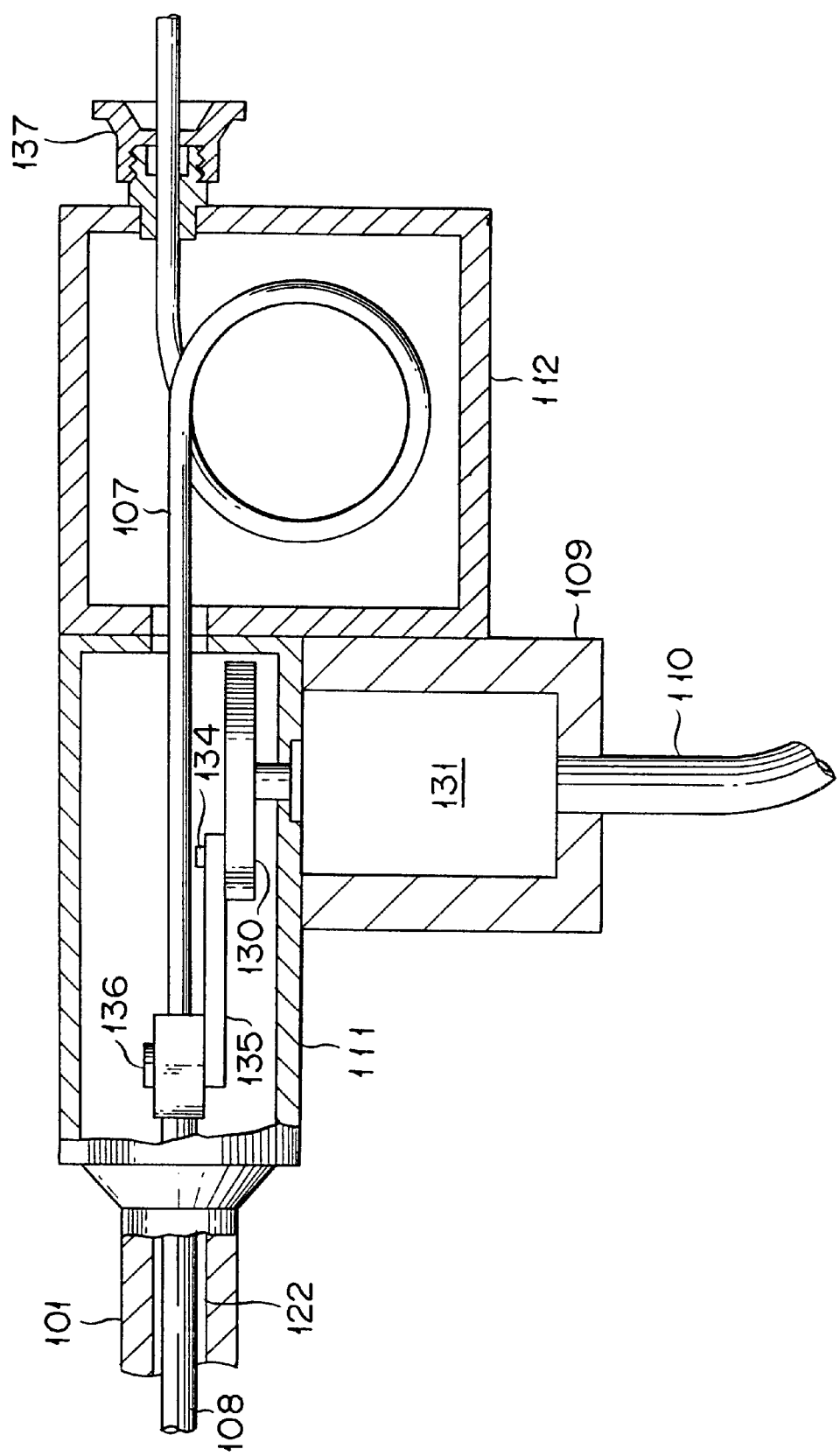
FIG. 8 is a partially cutaway side view of the cam box, a drive unit and a buffer device of the laser irradiation apparatus.
Figure 9A:
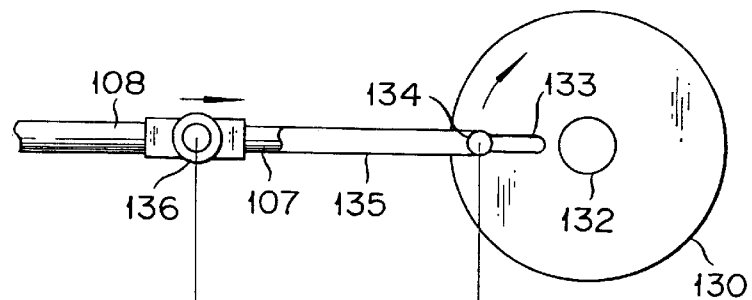
FIG. 9A–FIG. 9D are plan views of assistance in explaining the reciprocating motion of an optical fiber of the laser irradiation apparatus.
Figure 9B:
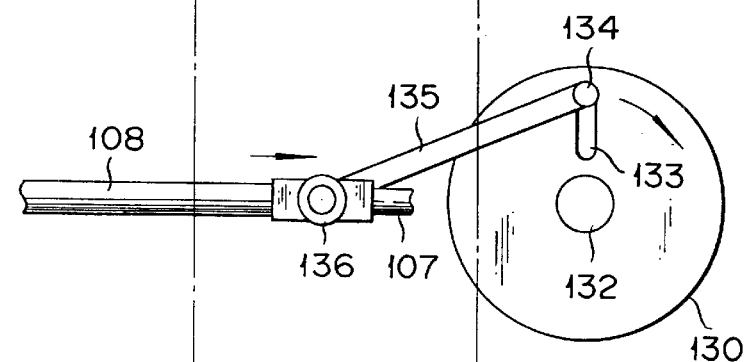
Figure 9C:
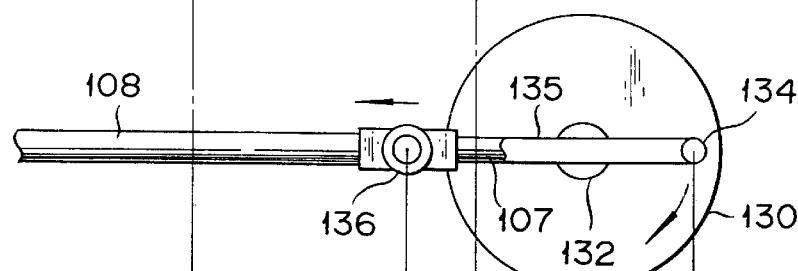
Figure 9D:
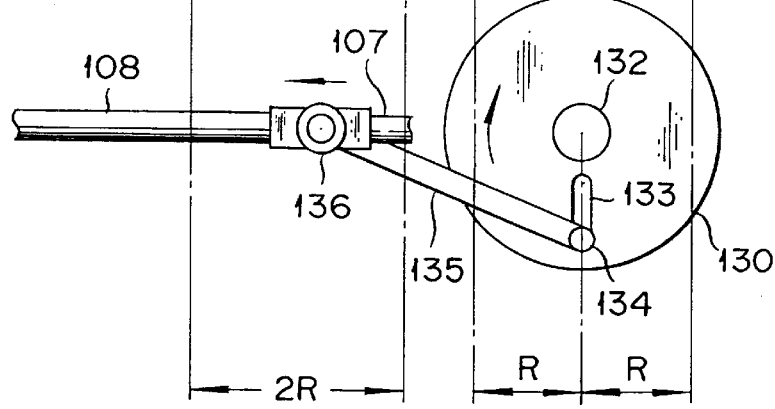

Next, the cam box 111, the drive unit 109 and the buffer device 112 will be described referring to FIG. 7 and FIG. 8.

The optical fiber 107, which is covered by the protection pipe 108 and is slidably supported by a lumen 122 of the main body 101, extends through the cam box 111 to the buffer device 112. The drive unit 109 includes an electrical cable 110 and a motor 131. The rotating motion of the motor is converted to a reciprocating motion by means of a cam stored in the cam box 111 and reciprocates the optical fiber 107.

The cam box 111 has a rotor 130 and a rod 135. The rotor 130 has a shaft 132 that is connected to the shaft of the motor 131 of the drive unit 109 and a groove 133 that is formed on the surface thereof in the radial direction. One end of the rod 135 is connected to a joint 134 in a pivot-like fashion. The joint 134 is positioned in the groove 133 and is fastened to the rotor 130 with a screw member. In other words, the rotor 130 is connected to one end of the rod 135 through the joint 134 with the screw member.

The other end of the rod 135 is connected to a joint 136 in a pivot-like fashion. The joint 136 is connected to the protection pipe 108 covering the optical fiber 107. In other words, the other end of the rod 135 grips the protection pipe 108 through the joint 136 in order to reciprocate the protection pipe 108 and the optical fiber 107.

The range of reciprocation of the optical fiber 107 can be adjusted by moving the fixing position of the joint 134. The protection pipe 108 ends at the proximal side of the joint 136.

The buffer device 112 is provided to prevent the optical fiber 107 from moving wildly on the outside of the apparatus 100. The buffer device 112 is provided with an opening that introduces the optical fiber 107 from the cam box 111 and a proximal part 137 that has another opening that leads the optical fiber 107 to the outside of the apparatus 100. The optical fiber 107 is stored forming a loop in the buffer device 112 and is fixed to the proximal part 137 as well. Therefore, the reciprocating motion of the optical fiber 107 is converted to the expansion and contraction motion of the loop inside the buffer device 112. In other words, the motion and load of the optical fiber 107 are absorbed, and the optical fiber 107 remains stationary on the outside of the apparatus 100.

Now, the mechanism of the reciprocating motion of the optical fiber 107 is described referring to FIG. 9A through FIG. 9D. For the sake of clarity in the description, a portion of the optical fiber 107 is not shown in the drawing.

When the rotor 130 rotates around the shaft 132 driven by the motor 131, the joint 134 fixed on the rotor 130 also rotates. However, the connection between the joint 134 and the rod 135 as well as the connection between the rod 135 and the joint 136, which is gripping the protection pipe 108, are pivot type connections. As a result, the protection pipe 108 and the optical fiber 107 moves in the axial direction of the main body 101. In other words, as the rotor 130 rotates around the shaft 132, the optical fiber 107 repeats the reciprocating motion in the axial direction of the main body 101 between the position shown in FIG. 9A and the position shown in FIG. 9C. Therefore the stroke of the optical fiber 107 and the stroke, or the moving range, of the reflector 113 that reciprocates accompanied by the optical fiber 107 is equal to twice the rotating radius R of the joint 134.

Figure 10:
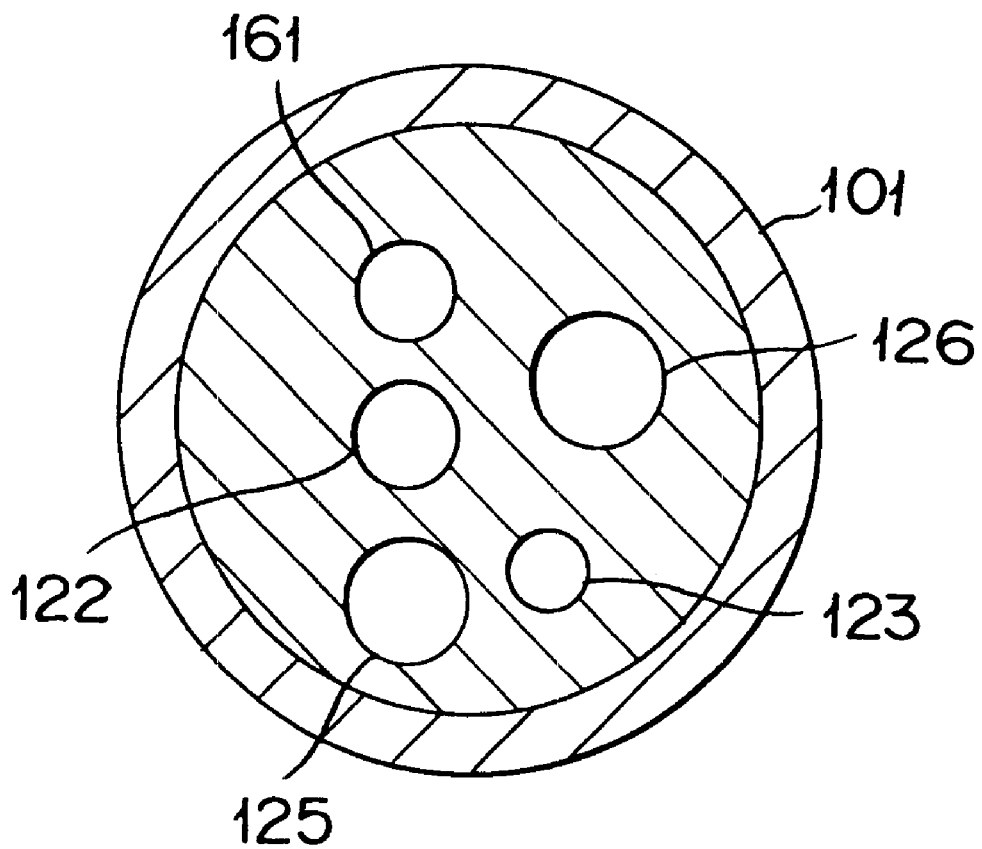
FIG. 10 is a cross sectional view taken on line X—X of FIG. 2.

Next, the cross sectional construction of the main body 101 will be described referring to FIG. 10.

Lumens 122, 123, 125, 126 and 161 are formed inside the main body 101. The lumen 122 is parallel to the axis of the main body 101 and the optical fiber 107 covered by the protection pipe 108 is inserted in it in such a way as to be able to reciprocate. At the proximal side of the lumen 122 is provided an O-ring (not shown) to prevent the leakage of the cooling liquid between the protective pipe 108 and the lumen 122.

The lumen 123 is used for the endoscope 124. Moreover, there is an opening on the bottom side of the lumen 123 as shown in FIG. 3 at a point where the wall member 151B is located. Therefore, it Is possible to observe the surface of the vital tissue, which is being irradiated with the laser ray, using the endoscope 124.

The lumens 125 and the lumen 126 are for the intake and discharge purposes of the cooling liquid. The lumen 125 and the lumen 126 are connected to the cooling liquid circulating device (not shown) via the tubes 105 and 106 shown in FIG. 1. Moreover, the lumen 125 communicates with the inner space where the reflector 113 is placed (see FIG. 2 and FIG. 3). Although the lumen 126 is not shown in FIG. 2, it also communicates with the inner space. Therefore, the cooling liquid supplied from the cooling liquid circulating device is introduced into the inner space of the distal end of the main body 101 via the tube 105 and the lumen 125, in order to cool the tissue surface, which is irradiated by the laser ray, and equipment components such as the laser emitting unit and the cover 104, through which the laser ray passes. The cooling liquid then returns to the cooling liquid circulating device through the lumen 126 and the tube 106. It is preferable to have check valves at the proximal ends of the lumens 125 and 126 to prevent the backflow of the cooling liquid.

The lumen 161 is used for connecting the balloon 103 and the port 160. Therefore, the liquid supplied through the port 160 is introduced into the balloon 103 through the lumen 161 to expand the balloon 103. The supply of the liquid is executed using a feeding device such as syringe or indeflator.

Next, the details of the endoscope 124 will be described.

The endoscope 124 (not shown) has an optical fiber bundle for image guide, an optical fiber for light guide, a protective tube, and an imaging lens provided at the distal end, and is installed in the apparatus in such a way as to be able to move freely in and out. More specifically, the endoscope 124 is inserted into the lumen 123 via an insertion port 127 (refer to FIG. 1), which is provided at the proximal end of the apparatus 100 and can fix the endoscope 124. By fixing the endoscope 124 at the insertion port 127, the distal end of the endoscope 124 can be located at a position within the main body 101 suitable for the observation. The bottom side of the lumen 123 is opened at the position where the wall member 151B is located (refer to FIG. 3). Therefore, the surface of the tissue, which is irradiated with the laser ray, can be observed using the endoscope 124. In other words, the positioning of the window 150 and the laser irradiation position can be visually confirmed based on the endoscope observation. Furthermore, it enables to optimize the irradiation condition based on the actual condition as the laser irradiation and the tissue surface observation can be performed simultaneously.

Next, the practical usage condition and the effect of the apparatus 100 will be described.

First, the distal end of the main body 101 is inserted into the urethra as shown in FIG. 6 and the window 150 for the laser emitting provided at the distal end is positioned in the vicinity of the target site 121 of the prostate 120, which is the lesional region to be treated. It is preferable to confirm the position of the window 150 directly using the endoscope 124. Next, while continuing the observation by the endoscope 124, the position of the laser emitting unit against the target site 121 is adjusted by moving the entire apparatus 100 in the longitudinal direction of the main body 101 or rotating the entire apparatus 100 manually.

Next, the balloon 103 is filled with liquid introducing it through the port 160 using the feeding device to expand the balloon 103. The cooling liquid circulating device starts to circulate the cooling liquid in the apparatus 100. More specifically, the cooling liquid flows into the inner space of the distal end of the main body 101 through the tube 105 and the lumen 125, and cools various components of the main body 101 and the surface of the vital tissue in close contact with the cover 104 which are being heated by the laser ray.

The side of the main body 101, where the balloon 103 does not exist and where the window 150 is formed, is fixed to and in close contact with the surface of the urethra, or the vital tissue. In other words, the positional relation between the laser emitting unit and the target site is fixed as the operator intended. Since the target site of the tissue is located at the prescribed direction and the depth, it is irradiated with the laser ray with certainty. The surface layer of the tissue in contact with the cover 104 and its vicinity is protected by the cooling liquid from heating, and the surface layer is protected from the related damage with certainty.

When the position is fixed, the motor 131 and then the laser generator start. The laser ray generated by the laser generator enters the reflector 113 via the optical fiber 107. The reflector 113 reflects the laser ray to sideways. The reflected laser ray is irradiated on the target site 121 in the prostate 120 through the window 150 of the main body 101. As the reflector 113 changes its reflecting angle as it travels back and forth axially accompanied by the optical fiber 107 at a frequency of 0.1–10 Hz, the path of the laser ray changes continuously but all the paths cross at the target site 121.

Thus, the target site 121 in the prostate 120 and its vicinity are heated by the laser ray to reach the desired temperature. On the other hand, a total amount of the laser irradiation at an area above the target site 121 in FIG. 6, for example, an arbitrary point in the surface layer of the prostate 120, is small so that the heat generated is limited. Likewise, a total amount of the laser irradiation at an area below the target site 121, or an area far away from the main body 101, is small so that the heat generated is limited.

In other words, the regions surrounding the target site 121 receive only a limited effect from the laser ray and are maintained at relatively low temperatures. This laser irradiation apparatus 100 offers high effect of treatment to the patient because damage to the regions other than the target site 121 are prevented or reduced. It is particularly advantageous as the surface layer damages are prevented even when the target site 121 is located at a position deep inside the vital tissue.

Next, the target site 121 is changed in the prostate 120 and the laser irradiation is executed again. By repeating this cycle as many times as needed, the prostate 120 consisting of multiple sites to be treated can be heated.

The laser rays used can be anything as long as they have deep penetration capabilities, but it is preferable that the laser rays have the wavelengths of about 750–1300 nm or 1600–1800 nm. It is because the laser rays can penetrate more effectively into living organisms at those wavelengths. In other words, the surface layer of the tissue absorbs only a little amount of the energy of the irradiated laser rays, so that they can be irradiated more effectively on the target site existing in the deeper region of the tissue.

Gas lasers such as He—Ne lasers, solid lasers such as Nd-YAG lasers, and semiconductor lasers such as GaAlAs lasers can be used as devices for generating laser rays with the wavelength mentioned above.

Structural materials for the wall members 151 can be a polymer alloy containing at least one of the followings or a polymer material including a plurality of ingredients from the followings: polyolefins such as polyethylene and polypropylene; ethylene-vinyl acetate copolymer (EVA); polyvinyl chloride; polyester such as polyethylene terephthalate and polybutylene terephthalate; polyamide; polyurethane; polystyrene; polycarbonate; and fluorocarbon resin.

The surface of the main body 101 or the balloon 103 can be coated with lubricating materials such as hydrophilic polymer materials, silicon and fluorocarbon resin. They will reduce the surface frictions of the components to be inserted into body cavities, and make it smoother to insert the main body 101 into body cavities. It is also possible to use a throwaway sheath to cover the main body 101 and apply lubricating coating to the sheath surface. The potential shortcoming of deterioration of lubricating capability due to wear after a plurality of uses can be prevented by means of using a throwaway sheath.

Hydrophilic polymers that can be preferably used for lubrication coating include: carboxymethyl cellulose, polysaccharide, polyvinyl alcohol, polyethylene oxide, sodium polyacrylate, methylvinylether-maleic anhydride copolymer, and water soluble polyamide. Of these, methylvinylether-maleic anhydride copolymer is most preferable.

When a laser irradiation apparatus equipped with a main body 101 and a balloon 103 coated with a hydrophilic polymer is used, the main body 101 and the balloon 103 are immersed into physiological saline before its use. This brings wetness and hence lubricity to the surface layers of the main body 101 and the balloon 103. For example, insertion of the main body 101 into a body cavity or its extraction from a body cavity or its transportation and rotation within a body cavity can be performed more smoothly. In other words, the friction resistance of the main body 101 and the balloon 103 to the vital tissue is reduced to lighten the burden of the patient and improve the effect of treatment to the patient.

The cover 104 should preferably be made of materials with excellent optical transmissivity such as PET (polyethylene terephthalate), quartz glass, acrylic resin, polystyrene, polycarbonate, polyethylene, polypropylene, vinylidene chloride, fluorocarbon resin, and polyester.

As described in the above, in the laser irradiation apparatus in accordance with the invention, the laser emitting position moves continuously while concentrating the laser ray on the target site in the lesional region. Consequently, vital issues other than the target site are kept at low temperatures and their damages can be prevented or reduced. It is particularly advantageous providing high effect of treatment to the patient as the surface layer damages are prevented even when the target site is located at a position deep inside a vital tissue.

Moreover, since the laser emitting unit reciprocates accompanied by the optical fiber, the relative positional relation between the optical fiber tip and the reflector is maintained approximately constant. As a result, it is possible to stabilize the spot diameter of the laser ray without using a special optical system. In addition, since the apparatus has a simple structure, it is easy to manufacture and its probability of trouble is small.

It is obvious that this invention is not limited to the particular embodiments shown and described above but may be variously changed and modified without departing from the technical concept of this invention.

This application is based on Japanese Patent Application No. 11-228960 filed on Aug. 13, 1999, the contents of which are hereby incorporated by reference.

What is claimed is:

1. A laser irradiation apparatus comprising: a long and slender main body;
   an optical fiber provided slidable inside said main body, having a proximal end through which a laser ray is introduced and a distal end through which the laser ray is emitted;
   a drive unit for causing said optical fiber to reciprocate in a longitudinal direction of said main body; and
   a reflector having a reflection plane for reflecting the laser ray emitted from said distal end of said optical fiber for reciprocating together with said optical fiber, being connected to said optical fiber; a reflecting angle of said reflection plane changing in accordance with the reciprocating motion of said optical fiber, wherein paths of the laser ray reflected by said reflection plane cross at a specified point regardless of the position of said reflector.

2. A laser irradiation apparatus as claimed in claim 1, wherein the sum of an incident angle and a reflecting angle of the laser ray relative to said reflection plane is less than 90 degrees when said reflector is located at a distal position, and is more than 90 degrees when said reflector is located at a proximal position.

3. A laser irradiation apparatus as claimed in claim 1, wherein said reflector has a protrusion and said main body has a guide groove for guiding movement of said protrusion.

4. A laser irradiation apparatus as claimed in claim 3, wherein said guide groove is non-parallel to an axial direction of said main body.

5. A laser irradiation apparatus as claimed in claim 1, further comprising:
   a guide for stabilizing behavior of the reciprocating motion of said optical fiber and said reflector.

6. A laser irradiation apparatus as claimed in claim 5, wherein said guide has a guide groove, which is parallel to an axial direction of said main body.

7. A laser irradiation apparatus as claimed in claim 6, wherein said guide further comprises a guide groove, which is not parallel to the axial direction of said main body.

8. A laser irradiation apparatus as claimed in claim 1, wherein said reflector is connected to said optical fiber via a hinge mechanism.

9. A laser irradiation apparatus as claimed in claim 8, wherein said hinge mechanism has a protrusion formed on a side of said reflector and an arm that can rotate around said protrusion.

10. A laser irradiation apparatus as claimed in claim 9, wherein said main body has a guide groove parallel to an axial direction of said main body for guiding movement of said arm.

11. A laser irradiation apparatus comprising:

an elongated main body;

an optical fiber slidably disposed inside the main body and having a proximal end through which a laser ray is introduced and a distal end through which the laser ray is emitted;

a drive unit operatively connected to the optical fiber to effect reciprocating movement of the optical fiber in a longitudinal direction of the main body;

a reflector having a reflection plane for reflecting the laser ray emitted from the distal end of the optical fiber, the reflector being operatively connected to the optical fiber to reciprocate together with the optical fiber; and means for causing the reciprocation of the reflector to change a reflecting angle of the reflection plane.

12. A laser irradiation apparatus as claimed in claim 11, wherein a sum of an incident angle and a reflecting angle of the laser ray relative to the reflection plane is less than 90 degrees when the reflector is located at a distal position and is greater than 90 degrees when the reflector is located at a proximal position.

13. A laser irradiation apparatus as claimed in claim 11, wherein paths of the laser ray reflected by the reflection plane cross at a specified point regardless of a position of the reflector.

14. A laser irradiation apparatus as claimed in claim 11, wherein the means for causing the reciprocation of the reflector to change a reflecting angle of the reflection plane comprises first and second pairs of guide grooves and first and second pairs of protrusions, each of the protrusions engaging one of the guide grooves.

15. A laser irradiation apparatus as claimed in claim 14, wherein one of the guide grooves is parallel to an axial direction of the main body and the other guide groove is nonparallel to the axial direction of the main body.

16. A laser irradiation apparatus as claimed in claim 14, wherein the guide grooves are formed in the main body.

17. A laser irradiation apparatus as claimed in claim 14, wherein the reflector is connected to the optical fiber via a hinge mechanism.

18. A laser irradiation apparatus as claimed in claim 14, wherein the first and second pairs of protrusions are provided on the reflector.

19. A laser irradiation apparatus as claimed in claim 14, wherein the protrusions constituting the first pair of protrusions are positioned on opposite sides of the reflector and the protrusions constituting the second pair of protrusions are positioned on opposite sides of the reflector.

* * * * *